(12) United States Patent
Ishihara (10) Patent No.: US 6,358,471 B1
(45) Date of Patent: Mar. 19, 2002

(54) AUTOMATIC MEASURING APPARATUS

(75) Inventor: Narihito Ishihara, Kanagawa (JP)

(73) Assignee: Tosoh Corporation, Shinnanyo (JP)

( * ) Notice: Subject to any disclaimer, the term of this patent is extended or adjusted under 35 U.S.C. 154(b) by 0 days.

(21) Appl. No.: 09/359,662

(22) Filed: Jul. 26, 1999

(30) Foreign Application Priority Data

Jul. 31, 1998 (JP) .......................................... 10-217201

(51) Int. Cl.[7] .......................... G01N 21/00; G01N 31/00; G01N 1/10; B01L 3/02
(52) U.S. Cl. ........................... 422/65; 422/100; 422/63; 422/64; 436/180; 73/864.01; 73/864.11
(58) Field of Search .................................. 422/100, 105, 422/63, 65, 64, 67, 68.1; 436/180; 73/864, 864.01, 864.11

(56) References Cited

U.S. PATENT DOCUMENTS

| | | | | |
|---|---|---|---|---|
| 4,451,433 A | * | 5/1984 | Yamashita et al. | 422/63 |
| 4,678,752 A | * | 7/1987 | Thorne et al. | 435/291 |
| 4,692,308 A | * | 9/1987 | Riley et al. | 422/65 |
| 4,864,848 A | * | 9/1989 | Irvine | 73/45.4 |
| 5,008,082 A | * | 4/1991 | Shaw | 422/65 |
| 5,178,834 A | * | 1/1993 | Kagayama et al. | 422/65 |
| 5,314,825 A | * | 5/1994 | Wreyrauch et al. | 436/43 |
| 5,350,052 A | * | 9/1994 | Gebald et al. | 198/465.2 |
| 5,482,861 A | * | 1/1996 | Clark et al. | 436/48 |
| 6,086,827 A | * | 7/2000 | Horner et al. | 422/102 |
| 6,096,561 A | * | 8/2000 | Tayi | 436/518 |
| 6,105,636 A | * | 8/2000 | Scatizzi et al. | 141/130 |
| 6,193,933 B1 | * | 2/2001 | Sasaki et al. | 422/64 |

* cited by examiner

Primary Examiner—Jill Warden
Assistant Examiner—Brian R Gordon
(74) Attorney, Agent, or Firm—Oblon, Spivak, McClelland, Maier & Neustadt, P.C.

(57) ABSTRACT

An automatic measuring apparatus comprising an annular conveyor for conveying specimen receptacles each having a top opening and reaction receptacles each having a top opening in an intermixed manner, conveyance means for imparting a drive to the conveyor, dispensing means for acquiring a certain amount of specimen from the specimen receptacles and for discharging it into the reaction receptacles, and transfer means for transferring the dispensing means in both the horizontal and vertical directions, wherein a horizontally extending track of the dispensing means defined by the transfer means coincides with part of a receptacle conveyance track provided by the conveyance means.

9 Claims, 8 Drawing Sheets

FIG. 10 dispensing means and is discharged into the reaction receptacle. Accordingly, in cases where the specimen receptacles and the reaction receptacles are conveyed on different conveyors or other means as in the prior art, the distance of horizontal movement of the dispensing means from the specimen receptacle up to the reaction receptacle will be elongated and transfer means may also become complicated.

AUTOMATIC MEASURING APPARATUS

BACKGROUND OF THE INVENTION

1. Field of the Invention

The present invention relates to an automatic measuring apparatus for quantifying a trace component contained in a specimen such as blood, serum, blood plasma, urine, etc., through biochemical or immunological reactions for example.

2. Description of the Related Arts

Up until now, measuring apparatuses are known which convey specimens and reaction receptacles separately by use of different conveyors or turntables, during which process a certain amount of specimen is sucked and discharged into the reaction receptacles to cause required reactions and thereafter make measurements (see Japanese Patent Laid-open Pub. No. Hei3-51762 for example).

Such conventional apparatuses may suffer from requirement for two or more separate conveyors due to the separate conveyance of the specimen receptacles and the reaction receptacles by means of different conveyors or the like. This may result in an enlarged size of the apparatus, in higher manufacturing costs and in an increased number of moving parts, requiring periodical maintenance. The increase in the number of the conveyors or other moving parts may lead disadvantageously to an increase in the number of conveyance means for driving them as well as to requirement of complicated control thereof.

The full amount of the specimen within the specimen receptacle is not necessarily subjected to measurement, but rather a certain amount of specimen is ordinarily sucked by dispensing means and is discharged into the reaction receptacle. Accordingly, in cases where the specimen receptacles and the reaction receptacles are conveyed on different conveyors or other means as in the prior art, the distance of horizontal movement of the dispensing means from the specimen receptacle up to the reaction receptacle will be elongated and transfer means may also become complicated.

SUMMARY OF THE INVENTION

It is therefore the object of the present invention to provide an automatic measuring apparatus having reduced dimensions at lowered manufacturing costs, which minimizes the number of the moving parts for conveying the specimen receptacles and the reaction receptacles to thereby dispense with frequent maintenance.

Thus, the inventor has come to complete the present invention as a result of wholehearted investigation to achieve the above object. According to one aspect of the present invention there is provided an automatic measuring apparatus comprising an annular conveyor for conveying specimen receptacles each having a top opening and reaction receptacles each having a top opening in an intermixed manner, conveyance means for imparting a drive to the conveyor, dispensing means for acquiring a certain amount of specimen from the specimen receptacles and for discharging it into the reaction receptacles, and transfer means for transferring the dispensing means in both the horizontal and vertical directions, wherein a horizontally extending track of the dispensing means defined by the transfer means coincides with part of a receptacle conveyance track provided by the conveyance means.

The above and other objects, aspects, features and advantages of the present invention will become more apparent from the following detailed description with reference to the accompanying drawings.

BRIEF DESCRIPTION OF THE DRAWINGS

FIGS. GA and 6B illustrate, in top plan and in longitudinal section, respectively, the state of a sensor and the status of the sensor when neither specimen receptacles nor reaction receptacles are present on the conveyor.

DESCRIPTION OF THE PREFERRED EMBODIMENTS

The present invention will now be described in more detail by way of a preferred embodiment thereof, in which the automatic measuring apparatus of the present invention is applied to an automatic immunological measuring apparatus for measuring trace components within the specimen by utilizing immune reactions.

The embodiment of the present invention is generally illustrated in FIGS. 1 to 10.

Figure 1:
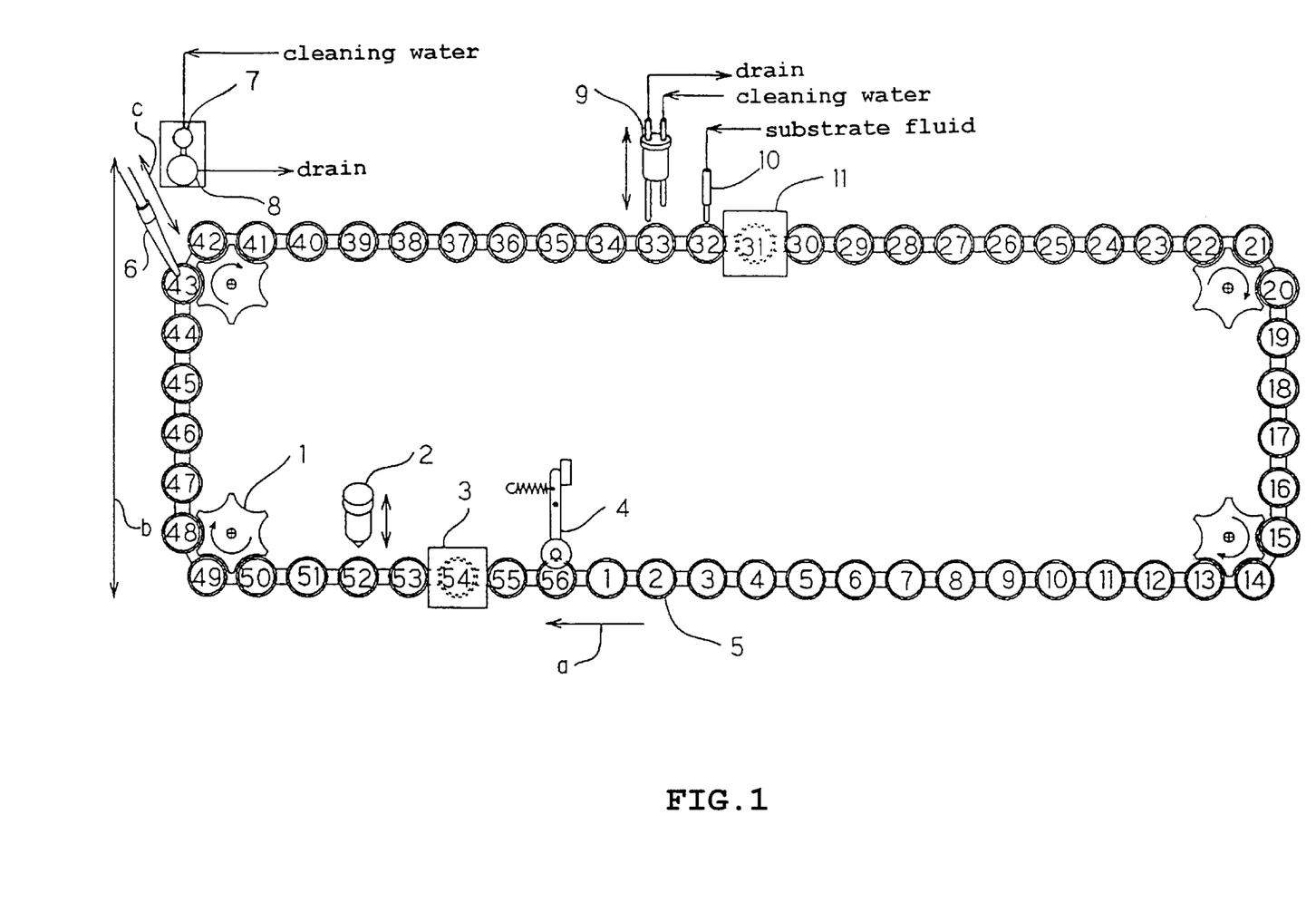
FIG. 1 is a diagram showing an embodiment of an automatic measuring apparatus of the present invention.

Referring first to FIG. 1, a conveyor is in the form of a substantially rectangularly deployed, annular endless track and is driven, in the direction indicated by an arrow a in the diagram, by conveyance means 1 connected to motors not shown. Under its driving force, specimen receptacles and reaction receptacles resting on the conveyor are conveyed in the direction of the arrow a.

No limitation is imposed on the conveyor as long as it can convey the specimen receptacles and the reaction receptacles in a mixed manner. It is however particularly preferred that the conveyor be able to convey the receptacles with fixed intervals therebetween in order to facilitate suction and discharge of the specimens effected by dispensing means. To keep the intervals between the receptacles constant, the conveyor can be provided thereon with for example recesses conforming to the external diameter (exterior contour) of the receptacles with fixed intervals.

The conveyance means 1 for driving the conveyor can be for example rollers or sprockets linked with the motors not shown. Use as the conveyance means of the sprockets having protrusions in particular allows engagement portions to be formed between the conveyor and the protrusions, preventing the conveyor from sliding when subjected to any load during its operations, which would otherwise place obstacles to the conveyance of the receptacles, to thereby ensure a secure conveyance of the receptacles. Although four sprockets are used in FIG. 1, all the sprockets need not be linked with the motors. For example, diagonally positioned sprockets may be driving ones, with two remaining sprockets being merely driven.

The conveyor, which will be described later, is capable of conveying a total of 56 specimen receptacles and reaction receptacles in this embodiment. Herein, the number of the conveyable receptacles is not particularly limited. Although the conveyor is of a rectangular form in FIG. 1, no restriction is offered to the form in which the conveyor is deployed. There could be employed for example an elliptical form ensuring easy configuration of the conveyor conveyance means. It is however particularly preferred that the conveyor have a rectilinearly driven section so as to allow a horizontally extending track of the dispensing means to coincide with a receptacle conveyance track as described later and that it have a rectangular or pentagonal form to ensure a smooth rotational movement of the conveyor.

In the diagram, reference numeral 6 denotes the dispensing means which, by a certain amount, suck a specimen from the specimen receptacle and discharge it into the reaction receptacle. The dispensing means are moved in horizontal and vertical directions by moving means not shown, with the arrangement being such that the horizontally extending track (indicated by an arrow b in the diagram) coincides partially with the receptacle conveyance track.

Figure 2A:
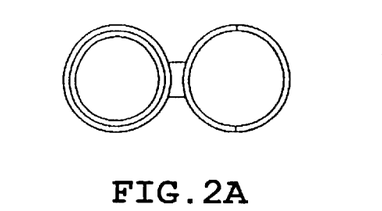
FIGS. 2A and 2B illustrate, in top plan and in longitudinal section, respectively, a basis component constituting a conveyor.
Figure 2B:
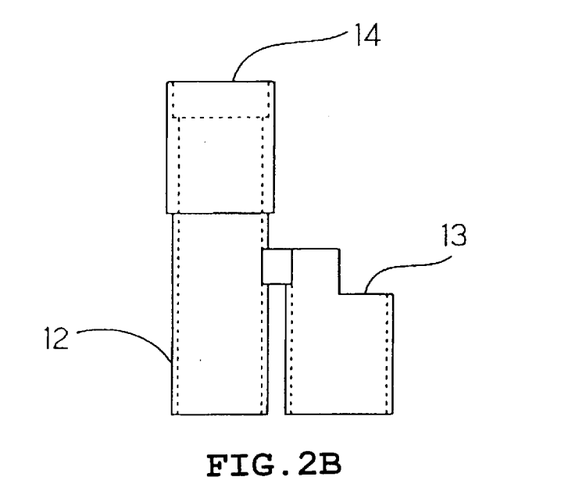
Figure 3:
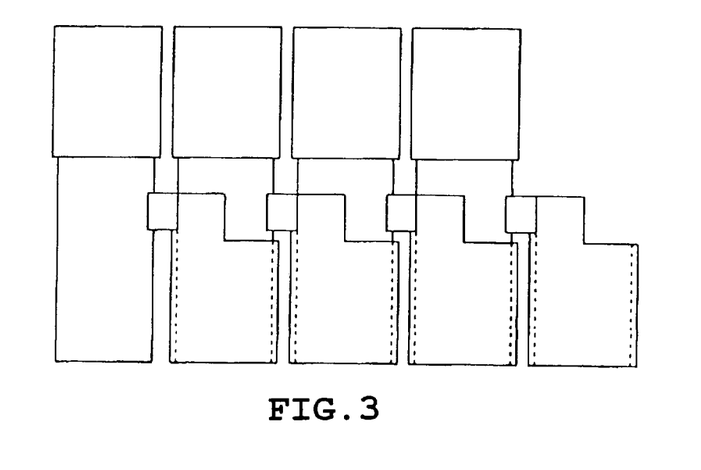
FIG. 3 is a diagram showing four basic components being coupled together.

FIGS. 2A, 2B and 3 depict basic components constituting the preferred conveyor of the present invention shown in FIG. 1. It is particularly preferred as described hereinabove that the conveyor be driven by use of the conveyance means with protrusions such as the sprockets and that the conveyor be provided thereon with the recesses conforming to the external diameter (exterior contour) of the receptacles to be conveyed. The conveyor meeting these requirements can be for example a conveyor which, as shown in FIGS. 2A and 2B, includes the basic components coupled to one another and each consisting of a cylindrical inserting part 12 and a cylindrical inserted part 13 which are formed integrally with each other. The basic components are coupled to one another such that the lower portion of the inserting part 12 is inserted and fitted into the inserted part 13 having a hollow portion shaped and dimensioned to receive the inserting part 12, to thereby form the endless track which, as shown in FIG. 3, has fixed intervals between the centers of the cylinders and is freely bendable in the horizontal direction at the joints. Herein, gaps defined between the lower portions of the inserting parts 12 and the inserted parts 13 form engagement portions with the protrusions of the sprockets 1 of FIG. 1. Hollow inserting parts 12 of the basic components would enable the hollow portions to be used as recesses for holding the specimen receptacles or the reaction receptacles.

Figure 4A:
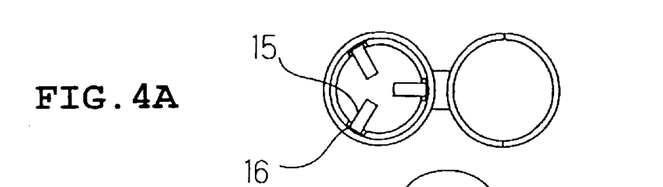
FIGS. 4A and 4B illustrate, in top plan and longitudinal section, respectively, the internal state of the basic component.
Figure 4B:
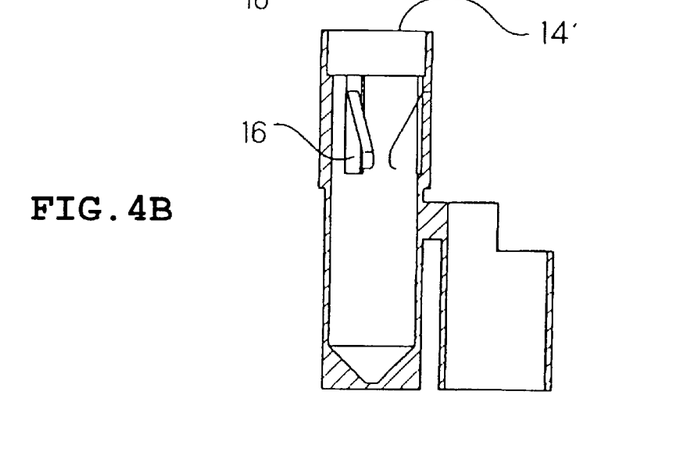
Figure 5A:
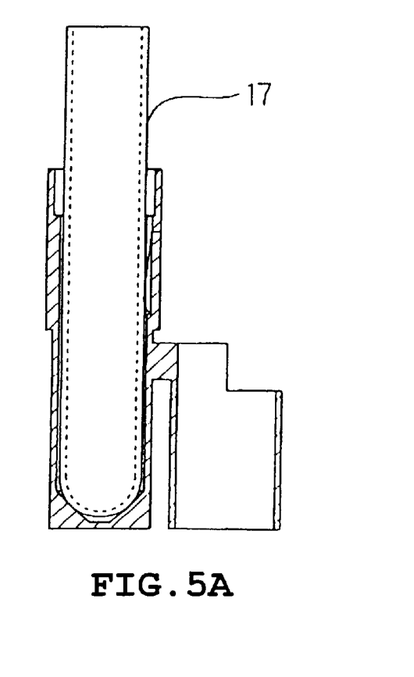
FIGS. 5A and 5B illustrate the state of resilient members when two different specimen receptacles having different external diameters are separately inserted into the hollow defined in the basis component.
Figure 5B:
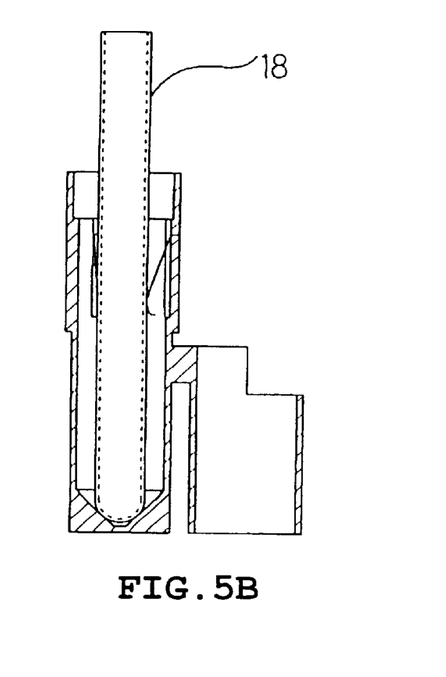
Figure 9A:
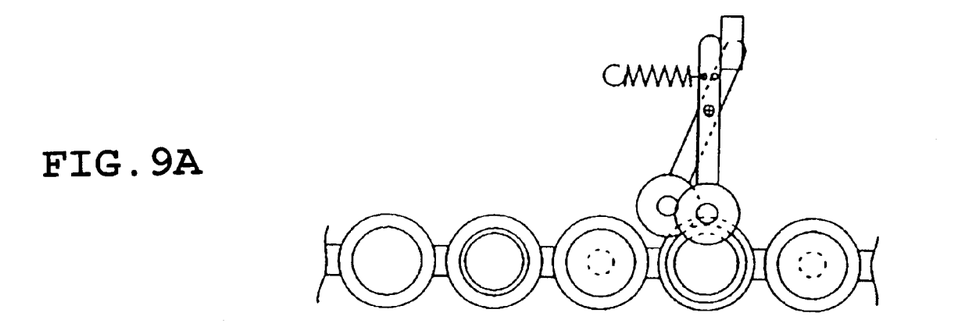
FIGS. 9A and 9B illustrate, in top plan and in longitudinal section, respectively, the state of a sensor and the status of the sensor when the specimen receptacles (cup-like) are present on the conveyor.
Figure 9B:
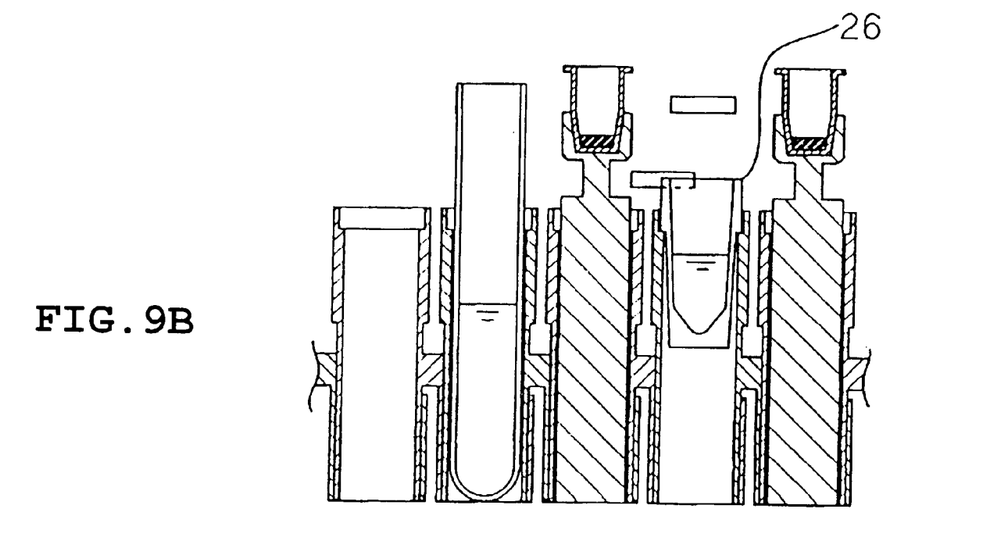

Referring then to FIGS. 4 and 5, there is depicted an example in which a hollow 14 is formed in the inserting part 12 of the basis component shown in FIGS. 2 and 3 and is used as the recess for holding the specimen receptacle or the reaction receptacle. These diagrams depict the basic component in section. The depth and opening diameter of the hollow portion 14 can appropriately be determined depending on the length and exterior contour of the specimen receptacle, reaction receptacle, etc., to be held. In the case of a cup-like receptacle having a broad brim, as shown in FIG. 9 for example, a stop for the brim may be formed in the vicinity of the opening of the hollow portion so that the receptacle can be held in the hollow portion by the abutment of the receptacle against the stop.

In case for example the specimen receptacles used have different external diameters, the bottom of the hollow portion 14 in the inserting part of the basic component is preferably provided with a conical slope so as to ensure that the receptacle when inserted is substantially centered in the hollow portion 14 of the inserting part. The specimen receptacles having different external diameters can be for example commonly used, vacuum blood sampling tubes having various external diameters, which are fed to the automatic measuring apparatus of the present invention. In addition to the impartment of the conical slope to the bottom in this manner, it is particularly preferred to provide resilient members 15 on the inner wall of the hollow portion 14. For attachment, the resilient members 15 can be for example fitted into grooves 16 formed in the wall surface of the hollow portion 14. In the case of holding a relatively thick receptacle 17 as shown in FIG. 5A the resilient members 15 are pressed against the inner wall, whereas with a relatively thin receptacle 18 as shown in FIG. 5B the receptacle is substantially centered in the hollow portion 14 by the cooperative actions of the slope and the resilient members. The resilient members may be plate-spring-like ones as shown, but instead they may be formed from rubber or the like, with the arrangement such that their respective actions cause the center of the receptacle to lie substantially at the center of the hollow portion 14.

Figure 8A:
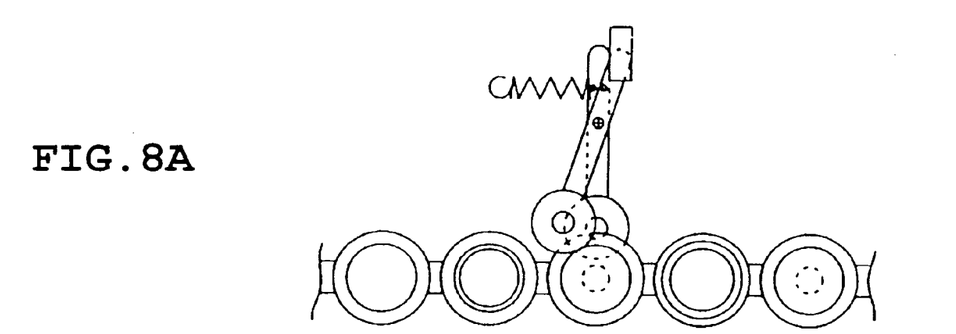
FIGS. 8A and 8B illustrate, in top plan and in longitudinal section, respectively, the state of a sensor and the status of the sensor when the reaction receptacles are present on the conveyor.
Figure 8B:
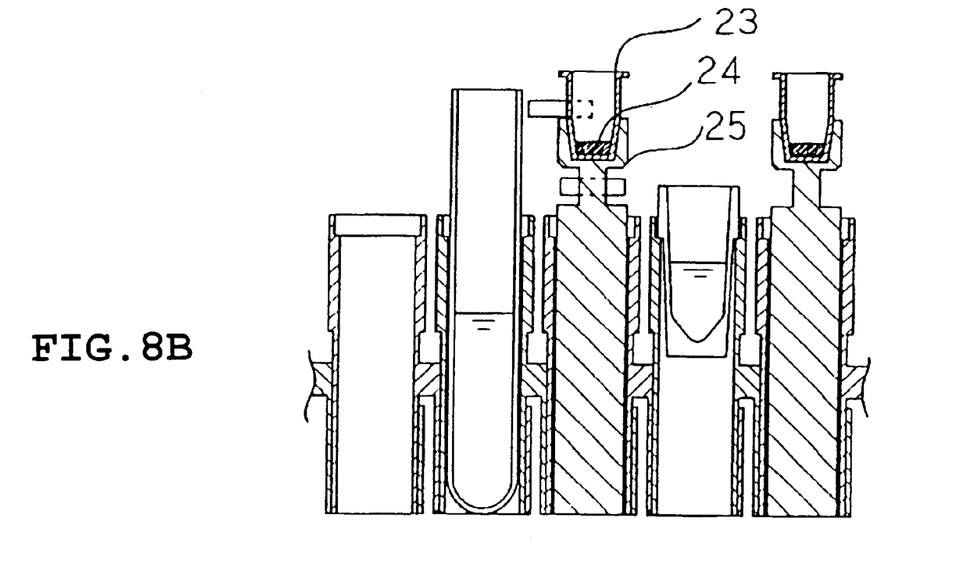

The specimen receptacle and reaction receptacle can be in the form of cylindrical tubes as shown in FIGS. 5A and 5B for example, although use may be made of cup-like receptacles 23 and 26 as exemplarily shown in FIGS. 8A, 8B and FIGS. 9A, 9B, respectively. In the case of using the cup-like receptacles, it is preferred for example that the hollow portion 14 in the inserting part 12 of each basic component of the conveyor have a depth matching the cup or that use is made of an adapter as shown in FIG. 8B and other figures, which consists of an upper part having a recess mating with the bottom surface of the cup and a lower part mating with the hollow portion 14. Conveniently, use of the adapter in particular allows two different type of receptacles, that is, relatively elongated receptacles and the cup-like receptacles to be used in an intermingled manner as exemplarily shown in FIGS. 6A and 6B and other figures. In this case, for example, by previously determining that the relatively elongated receptacles or the cup-like receptacles needing no adapters are used as the specimen receptacles and that the cup-like receptacles needing any adapters are used as the reaction receptacles, it would become easy to detect the type of the two receptacles on the basis of the geometries of the adapters as will be described later.

The substantially centering of the receptacle in the hollow portion 14 in the above embodiment aims to facilitate the control of movement of the dispensing means upon the subsequent suction and discharge effected by the dispensing means. To attain this aim, the receptacle need not necessarily be centered in the hollow portion, but instead the receptacle may be positioned such that it regularly comes into contact with the inner wall of the hollow portion. To this end, for example, the bottom of the hollow portion 14 may be made flat and a resilient member may be disposed so as to urge the receptacle in one direction and press it against the inner wall.

Although in FIG. 1 the dispensing means 6 are moved both in the horizontal direction (indicated by the arrow b in the diagram) and in the vertical direction (indicated by the arrow c in the diagram) by transfer means not shown, the present invention is characterized in that the horizontally extending track of the dispensing means indicated by the arrow b in the diagram coincides partially with the receptacle conveyance track provided by the conveyance means.

The dispensing means themselves can be hitherto known, either ones of a type (disposable type) having a disposable tip attachable to the nozzle and replacing the tip with new one for each suction and discharge of a different specimen for example, or ones of a type (permanent type) allowing a plurality of different specimens to be sucked and discharged without any replacement of the nozzle. The disposable type ones will be preferred from the viewpoint of eliminating any possibility of mutual contamination between the different specimens, whereas preference will be given to the permanent type ones in order to allow a simple configuration of the apparatus and to realize a reduction in production costs and a reduction in maintenance.

As is apparent from FIG. 1, in the case of employing the permanent type dispensing means, there are arranged cleaning means provided with a supply port 7 for nozzle cleaning water and a drain port 8 for automatically draining off the cleaning water contaminated by the specimen as a result of cleaning of the nozzle. The cleaning means are used to clean the nozzle before the suction and discharge of a different specimen, to thereby obviate any possible mutual contamination between the different specimens. It is particularly preferred that the cleaning means be disposed on an extended line of the receptacle conveyance track provided by the conveyance means of FIG. 1 and coinciding partially with the horizontally extending track of the dispensing means. Such a disposition will facilitate the horizontal movement of the dispensing means 6 and simplify the transfer means for the movement. On the contrary, in the case of employing the disposable type dispensing means described above, there must be arranged a disposal port for spent tips and an attachment port for new tips, both of which are also particularly preferably disposed on an extended line of the receptacle conveyance track provided by the conveyance means of FIG. 1.

Figure 10:
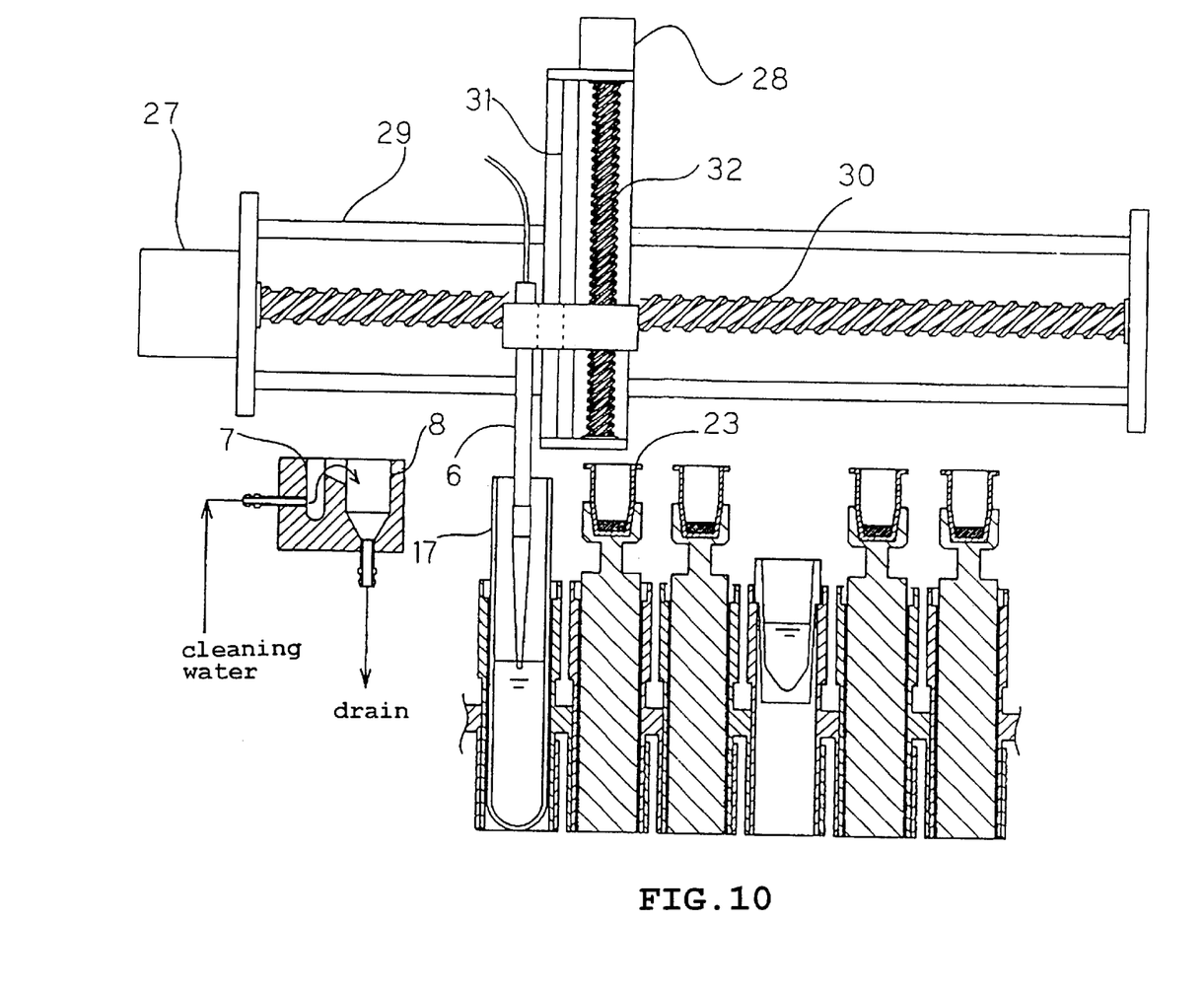
FIG. 10 is a diagram schematically showing dispensing means.

FIG. 10 illustrates by way of example the dispensing means, transfer means and cleaning means. The dispensing means 6 comprise a hollow nozzle whose one end is inserted into the specimen receptacle or the reaction receptacle for suction or discharge of the specimen. Negative pressure generation means can be for example a pump, and it is particularly preferred to use a syringe pump or other pump due to the necessity to suck and discharge a very small amount of specimen in $\mu l$ in the biochemical measurement.

The transfer means comprise a mechanism for moving the dispensing means 6 in the horizontal direction indicated by the arrow b of FIG. 1, and a mechanism for moving the dispensing means 6 in the vertical direction indicated by the arrow c of FIG. 1. Both the mechanisms could be conventional transfer means, although it is preferred to employ mechanisms having a feed screw as shown in FIG. 10 to provide a strict control of the amount of movement of the dispensing means and to ensure a correct movement.

In the example of FIG. 10, the mechanism for vertical movement includes a screw secured to a frame on which the dispensing means 6 are mounted, a feed screw 32 threaded into the screw, a motor 28 for turning the feed screw, and a vertical guide shaft 31, whereby rotation of the motor 28 causes the feed screw 32 to turn, allowing the dispensing means 6 to move vertically along the vertical guide shaft 31. The mechanism for horizontal movement on the other hand includes another screw secured to the frame, a feed screw 30 threaded into the screw, a motor 27 for turning the feed screw, and a horizontal guide shaft 29, whereby rotation of the motor 27 causes the feed screw 30 to turn, allowing the dispensing means 6 to move horizontally along the horizontal guide shaft 29.

In the example of FIG. 10, the cleaning means comprise a single block having two recesses, with cleaning fluid being fed from a tank not shown by a liquid feeding pump not shown to the cleaning fluid port 7. After the movement to above the cleaning means by the transfer means, the dispensing means 6 move in the vertical direction so that its nozzle is inserted through the cleaning fluid port 7. In this state the cleaning fluid is sucked and discharged to wash out the specimen adhered to the interior and exterior of the nozzle previous to the suction and discharge of the next specimen. On the other hand, the contaminated cleaning fluid is displaced toward the drain port 8 by newly fed cleaning fluid and is drained out of the cleaning means into a drain tank or the like.

In the present invention, the section of the receptacle conveyance track coinciding with the dispensing means track could be curvilinear, although it would particularly be preferred to be rectilinear as shown in FIG. 1 from the viewpoint of, e.g., achieving a simple apparatus configuration. In the case of the present invention, the suction and discharge by use of the dispensing means are carried out for receptacles resting on the track coinciding section, e.g., for six receptacles designated at 43 to 48 in the example of FIG. 1. The larger the number of receptacles lying on the track coinciding section is, the larger the number of reaction receptacles to be supplied with a specimen sucked from one specimen receptacle becomes. In the example of FIG. 1, the specimen can be sucked from one specimen receptacle and discharged into five reaction receptacles. Naturally, the five reaction receptacles may be ones having the same reagent sealed therein for measuring the same component in the specimen, or alternatively may be ones having two or more different reagents sealed therein for separately measuring two or more components in the specimen.

The reaction receptacle for use in the present invention can be for example one having a reagent sealed therein which reacts selectively with a specific component in the specimen. More concretely, in case the specific component is an antigen for example, the receptacle can be, by way of example, one having therein sealed (1) an antibody having an immunological specificity with the antigen and coupled to an insoluble carrier or (2) an antibody having an immunological specificity with the antigen and capable of being coupled to the antigen at a different position from that of the antibody of (1), the antibody being labeled either by a substance such as a luminous substance which itself can optically be measured or by a substance such as an enzyme allowing an indirect optical measurement. The above have been examples for carrying out a so-called sandwich measurement, but the other arrangement for making a competitive measurement could also be employed. The manner of sealing the reagent therein includes not only a case where the above antibodies or the like are present dissolved in an appropriate buffer solution for example, but also a case where the above antibodies or the like are present dried as designated at 24 in FIG. 8 through freezing and dehydration for example.

In any case, in the event of using the reaction receptacle containing the sealed-in reagent, the upper opening of the receptacle may often be covered with a seal foil of aluminum or the like. Thus, the automatic measuring apparatus of the present invention is provided along the conveyor with puncture means for puncturing such a seal foil if necessary. The seal foil may be marked with a symbol indicative of any component in the specimen to be measured by the reagent sealed in the reaction receptacle. Accordingly, the automatic measuring apparatus of the present invention is provided along the conveyor with identifying means for reading the symbol marked on the seal foil if needed. It will be appreciated that the identification means are disposed anterior to the puncture means, that is, upstream of the puncture means to read the symbol before the seal foil is punctured by the puncture means. The apparatus of FIG. 1 for example is shown provided with conically tapered puncture means 2 which are movable in the vertical direction, and with the identification means 3 disposed upstream of the puncture means 2, that is, on the upstream side in transport by the conveyor, for reading the symbol on the seal foil.

The identification apparatus 3 is not particularly limitative as long as it can read a symbol imparted on the seal foil and can identify the meaning expressed by the symbol. In other words, it can employ a concrete configuration in connection with the symbols. More specifically, there can be exemplified decoding of symbols by use of any symbols and camera (see Japanese Patent Laid-open Pub. No. Hei3-54470 for example) or combination of barcodes and a barcode reader in use.

In an immunological measurement or other measurement for example, the amount of specimen to be discharged into the reaction receptacle may possibly differ depending on components in the specimen to be measured. This is related to the lower and upper limits of detection in the measurement system using the reagent sealed in the reaction receptacle. In the automatic measuring apparatus of the present invention, as described above, the upper opening of the reaction receptacle is covered with the seal foil having thereon a symbol indicative of a reagent sealed in the reaction receptacle or a component with which the reagent reacts in a specific manner, and the identification means are disposed to identify the meaning of the symbol, whereby it is possible to provide an automatic measuring apparatus capable of automatically discharging an optimum amount of specimen by the dispensing means. To this end, it would be sufficient to dispose storage means for storing in a correlated manner symbols indicative of reagents or the like sealed in the reaction receptacles and the amount of specimen to be discharged into the reaction receptacles having the symbols thereon, as well as to provide such a control as to allow the specified amount of specimen to be sucked from the specimen receptacle and to be discharged into the reaction receptacle on the basis of the result of reading of the symbols by the identification means. A computer or other control means may be used to provide a control of, e.g., the storage means and of the pump connected to the dispensing means, whereby the amount of drive of the pump can be controlled through the arbitrary reading of the correlations stored in the storage means.

In the automatic measuring apparatus of the present invention as described hereinbefore, using the dispensing means the specimen is sucked from or discharged into receptacles lying on a track on which the horizontally extending track of the dispensing means defined by the transfer means coincides partially with the receptacle conveyance track defined by the conveyance means. It would therefore be preferred that the dispensing means be controlled to execute the suction, after positioning of the specimen receptacles from which the specimen is to be sucked at a predetermined point on the track for example. This control could be provided by use of a computer or other means, or alternatively by the control means arranged in conjunction with the storage means, for the control of the amount of drive of the pump.

In the case of the example of FIG. 1, the conveyance means are drive controlled so as to ensure that, at the stage when at least one component of a certain specimen to be measured has been determined, selection is made of one or more sorts of reaction receptacles each containing a reagent for measuring the component and that the thus selected reaction receptacles are placed downstream of the specimen receptacle on the conveyor, for example, the specimen receptacle is at all times placed at the position designated at 43 which is the most upstream position on the coinciding track whilst the reaction receptacles are placed downstream thereof, that is, at positions designated at 44 to 48. Alternatively, for example, instead of fixing the halt position of the specimen receptacle on the coinciding track, a predetermined amount of specimen may be discharged into the reaction receptacles, with the conveyor being rotated in the normal or reverse direction, while fixing the position at which the specimen sucked from the specimen receptacle is discharged into the reaction receptacles, to a position designated at 48 for example. On the contrary, the specimen receptacle may be at all times disposed at the position 48, upstream of which there are positioned the reaction receptacles each containing a sealed-in reagent or the like corresponding to a trace component to be measured. Although the control may become somewhat complex, the conveyance means may be so constructed as to be able to rotate in normal and reverse directions so that the specimen receptacle and the reaction receptacles can be placed entirely at random on the conveyor. Furthermore, in the example of FIG. 1, the coinciding track carries thereon only six receptacles, with the result that the arrangement permitting only one-directional movement of the conveyor allows the measurement to be performed only five times at most (since a total of six receptacles, i.e., one specimen receptacle and five reaction receptacles are only present on the coinciding track) However, by constructing the conveyance means so as to be rotatable in both normal and reverse directions, it is possible to restore the specimen receptacle lying out of the coinciding track to that coinciding track, thereby enabling the number of times of measurement to be increased.

More specifically, in cases where in the example of FIG. 1 the measurement is made of a specimen within any specimen receptacle using two sorts of reaction receptacles containing two different types of reagents sealed therein, the specimen receptacle is followed contiguously by such two sorts of reaction receptacles. Then, the specimen receptacle is conveyed to the position 43, after which the conveyance means 1 are deactivated and the dispensing means 6 are moved in the vertical direction so that the specimen is sucked therefrom by the total amount of the specimen to be discharged into the two sorts of reaction receptacles conveyed to the positions 44 and 45, the above total amount being invoked from the storage means on the basis of the symbols on the seal foils previously read by the identification means. Subsequently, the dispensing means are moved to the position 44 to discharge a predetermined amount of specimen into the reaction receptacle located at the position 44, and then further moved to the position 45 to discharge a predetermined amount of specimen into the reaction receptacle located at the position 45. Naturally, arrangement may be such that after discharge of a predetermined amount of specimen into the reaction receptacle located at the position 44, the dispensing means once return to the position 43 to again suck the specimen, and then move to the reaction receptacle located at the position 45 to discharge a predetermined amount of specimen thereinto. After the completion of such a series of operations, the next specimen receptacle is located at the position 43 and the same operations are iterated.

In the automatic measuring apparatus of the present invention, it is preferred to dispose, along the conveyor, level detection means for detecting the level of the specimen within the specimen receptacle, so as to control the distance of downward movement of the dispensing means in the vertical direction by the transfer means on the basis of the result of detection by the detection means so that the nozzle of the dispensing means is inserted into the specimen to a certain depth. In case of the arrangement causing the downward movement of the dispensing means in the vertical direction by a certain distance regardless of the specimen level, it will be anticipated that when the specimen level is lower than expected, the nozzle of the dispensing means may not reach the interior of the specimen and may be unable to suck the specimen, whereas when the specimen level is higher than expected, the nozzle of the dispensing means may be inserted into the interior of the specimen to a greater depth than required, which may result in adhesion of a large amount of specimen onto the external surface of the nozzle, or in dropping of droplets of the thus adhered specimen into the reaction receptacle, or when the permanent nozzle is employed, even in impossibility of cleaning the specimen adhered on the external surface of the nozzle. The specimen level detection means can be for example electrical detection means which always detect impedance at the nozzle to grasp any variation in the impedance which may occur as a result of contact of the nozzle with the specimen surface.

Separately from the output from the specimen level detection means, it is preferred to previously determine the lowering limit distance of the dispensing means in the vertical direction. This lowering limit distance depends on geometric configurations or the like of the specimen receptacles. For example, the specimen receptacle 17 shown in FIGS. 7A and 7B and the specimen receptacle 26 shown in FIGS. 9A and 9B have different distances through which the dispensing means can move in the vertical direction, as apparent from the diagrams. To this end, for example a sensor may be arranged for detecting the sorts of the receptacles as will be described hereinafter so that control is provided to select a previously defined lowering limit distance on the basis of the sort of the receptacle detected by the sensor outputs. By virtue of the previous determination of such a lowering limit distance, it will become possible to avoid any possible collision of the nozzle of the dispensing means with the bottom of the specimen receptacle, which may possibly occur in case a vacant specimen receptacle has erroneously been placed on the conveyor due to any operation miss.

Various sensors are arranged in order to provide the above described automatic measuring apparatus which automatically reads symbols on the seal foil covering the opening of the reaction receptacle and controls movement of the dispensing means to discharge a predetermined amount of specimen into the reaction receptacle. These sensors can include (1) a sensor for detecting whether any receptacle being conveyed on the conveyor is present or not (hereinafter, referred to as a first sensor), (2) a sensor for detecting the sort of a receptacle being conveyed on the conveyor, that is, whether it is a specimen receptacle or a reaction receptacle (hereinafter, referred to as a second sensor), and (3) a sensor for detecting that the thus detected receptacle, in particular the specimen receptacle has been conveyed to a predetermined position on a track on which the horizontally extending track of the dispensing means defined by the transfer means coincides partially with the receptacle conveyance track defined by the conveyance means (hereinafter, referred to as a third sensor).

The first sensor serves to prevent the dispensing means from attempting in vain to suck or discharge the specimen from or onto a conveyor section which carries no receptacles thereon. In the example of FIG. 1, a sensor 4 is disposed in order to attain this end.

The second sensor serves to detect whether the receptacle whose presence has been detected is a specimen receptacle or a reaction receptacle. In the example of FIG. 1, the sensor 4 acting also as the first sensor is disposed in order to achieve this object.

The third sensor serves to detect that the receptacle judged to be a specimen receptacle by the second sensor has been conveyed to and located at a position where sucking operation is effected by the dispensing means 6, such as the position 43 concretely shown in FIG. 1 for example. In the example of FIG. 1, this sensor is omitted, with the arrangement being such that the revolving angles of the sprockets 1 acting as the conveyance means are controlled by stepping motors for driving the sprockets, an oscillation circuit for imparting a drive signal to the stepping motors and a computer which provides a control of the oscillation circuit, and that if the receptacle detected by the sensor 4 is a specimen receptacle, the revolving angles of the sprockets are controlled so that the conveyance means come to a halt at the stage when that receptacle has reached the position 43.

In the fields of ordinary biochemical measurements and immunological measurements, as set forth hereinabove, the specimen may be introduced into cylindrical tubes 17 and 18, such as vacuum blood sampling tubes, having different external diameters as shown in FIGS. 5A and 5B, or otherwise, the specimen which is not introduced into such tubes may be introduced into the specimen receptacle 26 used exclusively for the automatic measuring apparatus as illustrated in FIGS. 9A and 9B by way of example, previous to being fed to the apparatus. As opposed to this, the reaction receptacle usually takes the form of a dedicated reaction receptacle for the automatic measuring apparatus as illustrated in FIGS. 8A and 8B for example. Thus, by shaping the dedicated reaction receptacle so as to be distinguished by its exterior contour from the specimen receptacle to be fed to the automatic measuring apparatus, it is possible to employ sensors having a simplified configuration as the first and second sensors.

As illustrated in FIGS. 6A and 6B to FIGS. 9A and 9B in greater detail, the sensor 4 in FIG. 1 for example serves to detect the state of contact with the receptacles, which have their respective exterior contours allowing the dedicated reaction receptacle 5 and specimen receptacle to be distinguishable from each other, to thereby achieve the above object. The sensor 4 is a contact-type sensor provided with a sensor lever which includes a roller part 22 having a rolling wheel at its tip. The sensor lever 4 is arranged to pivot around a fixed point 19 when the roller part 22 comes to contact with the receptacle, the sensor lever 4 being always urged by a spring 20 to be restored to a predetermined position. An optical transmission type sensor 21 is disposed in close vicinity to the other end of the roller part of the sensor lever 4 such that when a contact of the receptacle with the roller part 4 causes a pivotal movement of the sensor lever 4, the sensor transmitted light is shut out to detect the contact. Then, in the example of FIG. 1, the thus configured sensors are arranged on upper and lower sides thereof as illustrated in FIGS. 8A, 8B and 9A, 9B.

Figure 6A:
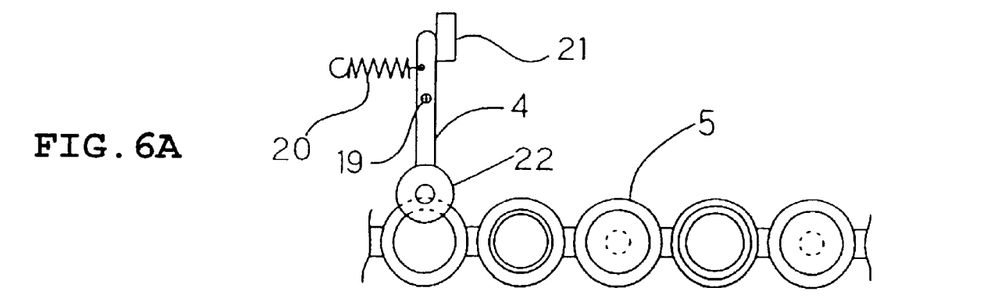
Figure 6B:
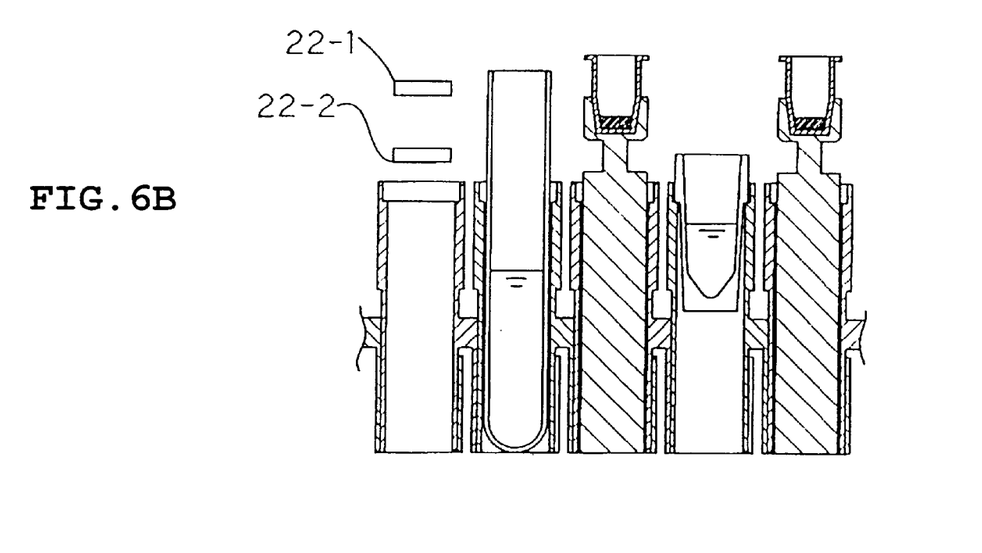
Figure 7A:
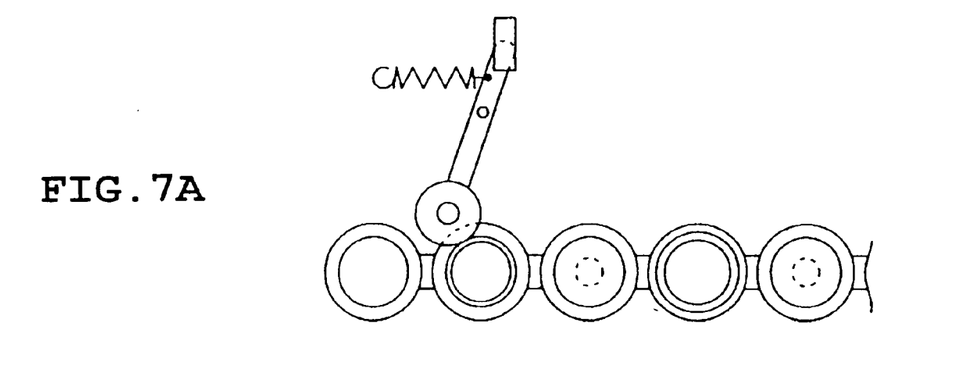
FIGS. 7A and 7B illustrate, in top plan and in longitudinal section, respectively, the state of a sensor and the status of the sensor when the specimen receptacles are present on the conveyor.
Figure 7B:
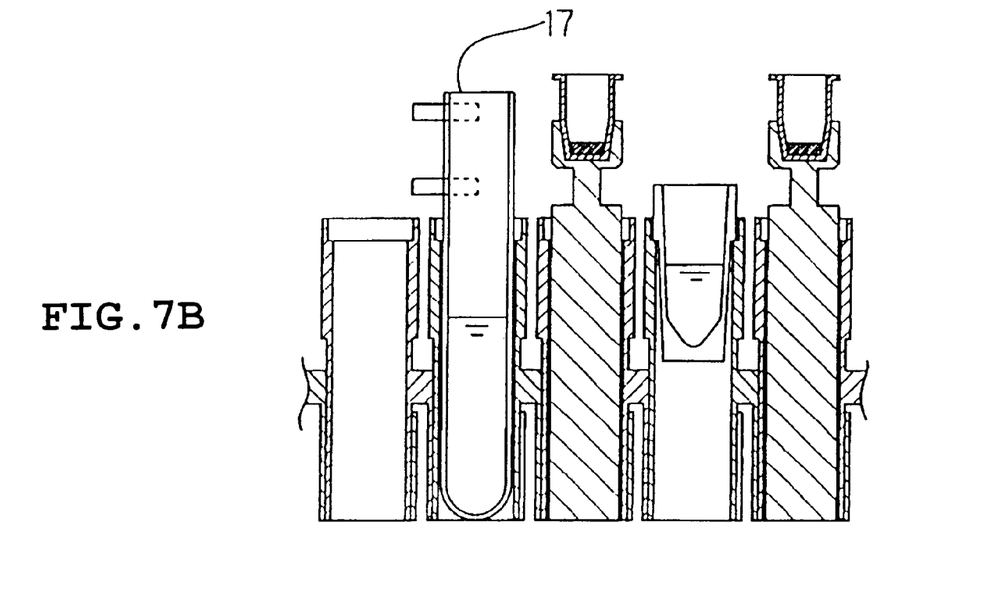

FIGS. 6A and 6B show the state of the sensor 4 when any receptacle is absent within the recesses on the conveyor. In such a case, a roller part 22-1 of the upper sensor and a roller part 22-2 of the lower sensor do not come to contact with the receptacle. In contrast with this, FIGS. 7A and 7B show the state when a cylindrical tube 17 (specimen receptacle) passes through the sensor 4. The cylindrical tube 17 is brought into contact with the roller parts 22-1 and 22-2 of the upper and lower sensors. Thus, in the example of FIG. 1, if both the sensors provide their respective outputs, the presence of the cylindrical tube, that is, the specimen receptacle can be detected. FIGS. 8A and 8B show the state where the dedicated reaction receptacle 23 is detected. The dedicated reaction receptacle is placed on the conveyor by way of an adapter used exclusively for the reaction receptacle in order to make definite the geometrical difference from the specimen receptacle. This adapter includes a recess for holding the reaction receptacle, a part fitting into the hollow (recess for holding the specimen receptacle) in the insertion part 12 in the basic component, and a neck in the form of a connection thinner than the widths of the recess and the fitting part, the neck having a concave section. Due to its neck, the connection does not come into contact with the roller part 22-2 of the lower sensor as shown in FIGS. 8A and 8B. However, the roller part 22-1 of the upper sensor is adjusted to have a height allowing a contact with the reaction receptacle. Accordingly, if the upper sensor provides an output without any output from the lower sensor, the presence of the reaction receptacle can be detected. FIGS. 9A and 9B show the state of detection of the dedicated specimen receptacle 26. The dedicated specimen receptacle is configured to be inserted into the hollow in the inserting part 12 of the basis component up to a height not allowing any contact with the roller part 22-1 of the upper sensor, in order to make definite the geometric difference from the reaction receptacle. Accordingly, if the lower sensor provides an output without any output from the upper sensor, the presence of the specimen receptacle other than the cylindrical tube can be detected. Such a dedicated specimen receptacle can be of a tapered bottom and maybe used to transfer the specimen thereinto as when normal suction of the specimen is difficult to perform due to a trace of specimen resulting in too low specimen level in the case of feeding in the ordinary cylindrical tube.

Other than the above, a reflection type sensor or a proximity sensor which reacts only on metal could be used as the sensor. In such a case, use may be made of a reaction receptacle having the outer periphery made of a lustered material, the reaction receptacle being detected by the optical reflection type sensor to be distinguishable from the specimen receptacle. In the case of the proximity sensor, a metal strip may be secured only to the outer periphery of the reaction receptacle for example. Furthermore, in the example of FIG. 1, the identification means could be replaced by the sensor. Thus, when using the reaction receptacle whose upper opening is covered with the seal foil, it is possible to discriminate the receptacle having an identified symbol on its seal foil from the other reaction receptacles.

In the case of disposing the various types of sensors, a computer or the like may be employed as the control means, which receive outputs from the sensors and judge patterns of the input signals to achieve the above object. It will be appreciated that such control means may be used with the other control means as set forth hereinabove. Then, if any receptacle is not detected as shown in FIGS. 6A and 6B, a warning may simply be issued to the operator and simultaneously the conveyance means, dispensing means, transfer means, etc., may come to a halt.

In the event that the automatic measuring apparatus of the present invention is to be applied to an measuring apparatus for measuring a specific trace component by use of a reagent containing a water-insoluble carrier in e.g., a dry immunological measurement method, it is preferred to dispose B/F separation means as shown in FIG. 1. The B/F separation is an operation for separating a component coupled to the carrier from the other components. In the example of the sandwich measurement described earlier, it is an operation with which, among the antibodies or the like labeled either by a substance such as a luminous substance which itself can optically be measured or by a substance such as an enzyme allowing an indirect optical measurement, ones coupled to the carrier by way of the trace component to be measured is separated from ones existing in a liberated manner. As can exemplarily seen in FIG. 1, the B/F separation means can be for example means equipped with two tubes, that is, a tube through which is supplied a cleaning fluid for cleaning the interior of the reaction receptacle, and a tube through which the liberated components is sucked from the interior of the reaction receptacle for drainage.

The automatic measuring apparatus of the present invention is further provided with detection means 1 for detecting a trace component to be finally measured or for performing that detection after the substitution of the component with an measurable substance. In the example of the sandwich measurement described hereinabove, the detection means 1 are used to detect antibodies labeled either by a substance such as a luminous substance which itself can optically be measured or by a substance such as an enzyme allowing an indirect optical measurement, the antibodies remaining within the reaction receptacle as a result of the B/F separating operation. Herein, if the detection target is a substance such as an enzyme allowing an indirect optical measurement, substrate dispensing means 10 are used to dispense, prior to the detection, an enzyme substrate having fluorescence or other property, which can be converted into another substance able to be detected by the action of that enzyme.

Other than the above, if for example the reaction receptacles need any incubation for a certain period of time under a fixed temperature condition after the discharge of the specimen, a heater and a temperature regulating circuit may be disposed with a heat insulating material which covers the conveyor at positions 34 to 42. In case of continuous measurements, management of the incubation time can be carried out by increasing or reducing the number of receptacles to be placed on the conveyor to thereby increase or reduce the number of receptacles positioned at sites corresponding to the positions 34 to 42. If for example ten min. incubation time is required with a simple conveyor drive control being one pitch per minute, it is sufficient to locate ten receptacles at the positions 34 to 42.

Furthermore, in the example of FIG. 1, it is preferred to conceal the top of positions 31 to 56 by a cover, with the aim of keeping the specimen receptacles and the reaction receptacles at a certain temperature, preventing any substances which may act on the measurement from entering the receptacles, and shutting out the external light which may affect the optical detection by the detection means 11. In this event, the specimen receptacles and the reaction receptacles can be placed on the conveyor at positions designated at 1 to 30, which are not concealed by the cover for example.

Immediately after the completion of the measurement, the associated specimen receptacles and reaction receptacles are removed, and instead other specimen receptacles and reaction receptacles newly subjected to the measurement are placed on the conveyor, whereby it is possible to perform continuous measurements without halting the apparatus. In cases where for example the upper opening of each reaction receptacle is covered with a seal foil, even though the operator has failed to remove the reaction receptacles whose measurements are complete, the identification means (designated at 3 in FIG. 1) or a sensor can detect the inadvertently remaining reaction receptacles, thereby preventing any possible erroneous measurements.

The automatic measuring apparatus of the present invention can advantageously simplify the transfer means as compared with the conventional apparatus, by conveying the specimen receptacles and the reaction receptacles by the same conveyance means such as a conveyor in an intermixed manner and by causing part of the track of the conveyor to coincide with the horizontally extending track of the dispensing means, unlike the prior art apparatus.

In consequence, it will be easy to reduce the dimensions of the apparatus of the present invention, with the reduction in the number of components resulting in lowered manufacturing costs, and with the reduction of the movable parts resulting in lowered frequency of periodical maintenance.

Advantageously, particularly preferred embodiment of the present invention will provide an automatic measuring apparatus having a higher throughput capacity, in which the operator has simply to place specimen receptacles and then reaction receptacles containing sealed-in reagents for use in the measurements in a contiguous manner so that measurements corresponding to the thus placed reaction receptacles are automatically carried out.

What is claimed is:

1. An automatic measuring apparatus comprising an annular conveyor for conveying specimen receptacles each having a top opening and reaction receptacles each having a top opening, wherein said specimen and reaction receptacles are intermixed along the conveyor, conveyance means for imparting a drive to said conveyor, dispensing means for acquiring a certain amount of specimen from said specimen receptacles and for discharging the specimen into said reaction receptacles, and transfer means for transferring said dispensing means in both the horizontal and vertical directions, wherein a horizontally extending track of said dispensing means defined by said transfer means coincides with part of a receptacle conveyance track provided by said conveyance means, further comprising a sensor for detecting the presence or absence of receptacles being conveyed on said conveyor and for detecting if the sorts of said receptacles are present, and a sensor for detecting that said receptacles detected to be present has been conveyed to a predetermined position on said coinciding part of said receptacle conveyance track, said two sensors being arranged along said conveyor.

2. An automatic measuring apparatus according to claim 1, wherein
said reaction receptacle contains a sealed-in reagent which reacts selectively with a specific component within said specimen.

3. An automatic measuring apparatus according to claim 1, wherein
said top opening of said reaction receptacle is covered with a seal foil, said apparatus further comprising puncture means for puncturing said seal foil, said puncture means being disposed along said conveyor.

4. An automatic measuring apparatus according to claim 3, wherein
said seal foil covering said top opening of said reaction receptacle is marked thereon with a symbol indicative of a reagent sealed in said receptacle or indicative of a specific component with which said reagent reacts selectively, said apparatus further comprising identification means for reading said symbol, said identification means being disposed upstream of said puncture means.

5. An automatic measuring apparatus according to claim 4, further comprising storage means for storing in a correlated manner said symbol indicative of a reagent sealed in said receptacle or indicative of a specific component with which said reagent reacts selectively, and the amount of specimen to be discharged into said receptacle,
wherein based on the result of reading of said symbol by said identification means, said dispensing means suck a specified amount of specimen from said specimen receptacle and discharge it into said reaction receptacle.

6. An automatic measuring apparatus according to claim 1, further comprising level detection means arranged along said conveyor, for detecting the level of specimen within said specimen receptacle, wherein based on the result of detection by said means, control is provided of the distance of downward movement of said dispensing means in the vertical direction achieved by said transfer means.

7. An automatic measuring apparatus comprising an annular conveyor for conveying specimen receptacles each having a top opening and reaction receptacles each having a top opening, wherein said specimen and reaction receptacles are intermixed along the conveyor, conveyance means for imparting a drive to said conveyor, dispensing means for acquiring a certain amount of specimen from said specimen receptacles and for discharging the specimen into said reaction receptacles, and transfer means for transferring said dispensing means in both the horizontal and vertical directions, wherein a horizontally extending track of said dispensing means defined by said transfer means coincides with part of a receptacle conveyance track provided by said conveyance means, wherein
said conveyor is in the form of an endless track having joints that allow said track to bend freely in the horizontal direction said conveyor including a plurality of basic components each consisting of a single cylindrical inserting part and a single cylindrical inserted part which are integrally formed, said inserting part of a basic component being inserted into said inserted part of another basic component for coupling to form said endless track, and wherein
said inserting part is hollow in its at least upper portion.

8. An automatic measuring apparatus according to claim 7, wherein
said specimen receptacle or said reaction receptacle is inserted into and retained in said hollow portion of said inserting part.

9. An automatic measuring apparatus according to claim 8, wherein
said hollow portion of said inserting part is provided with resilient members for retaining a receptacle having an external diameter smaller than the diameter of said hollow portion at a position where the center of said hollow portion substantially coincides with the center of said receptacle.

* * * * *